US00PP10251P

United States Patent [19]

VandenBerg

[11] Patent Number: Plant 10,251

[45] Date of Patent: Feb. 24, 1998

[54] CHRYSANTHEMUM PLANT NAMED 'SUNSET MADISON'

[75] Inventor: Cornelis P. VandenBerg, Salinas, Calif.

[73] Assignee: Yoder Brothers, Inc., Barberton, Ohio

[21] Appl. No.: 770,713

[22] Filed: Dec. 19, 1996

[51] Int. Cl.[6] ..... A01H 5/00

[52] U.S. Cl. ..... Plt./74.1

[58] Field of Search ..... Plt./74.1, 82.3

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutuation Breeding Methods inthe Improvement of Vegetatively Propagated Crops", Elsevier Sci, Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X–and gamma radiation", Euphytica, 15:204–210.

*Primary Examiner*—Howard J. Locker
*Attorney, Agent, or Firm*—C. A. Whealy

[57] ABSTRACT

A distinct cultivar of Chrysanthemum plant named 'Sunset Madison', characterized by its upright and mounded plant habit; medium-size daisy spray-type inflorescences that are 6.4 and 7.3 cm in diameter; attractive red and yellow bi-colored ray florets and bright yellow disc florets; and good postproduction longevity with inflorescences maintaining good substance and color for about 2.5 weeks in an interior environment.

1 Drawing Sheet

The present invention related to a new and distinct cultivar of Chrysanthemum plant, botanically known as *Dendranthema grandiflora* and referred to by the cultivar name Sunset Madison.

the new cultivar is a product of a mutation induction breeding program conducted by the inventor in Fort Myers, Fla., and Salinas, Calif. The objective of the breeding program is to create new Chrysanthemum cultivars having inflorescences with desirable inflorescence forms and floret colors and good post-production longevity.

The new cultivar originated by exposing 75 unrooted cuttings of the Chrysanthemum cultivar Madision (disclosed in U.S. Plant Pat. No. 9,313) to a radiation level of 1,500 rads in March, 1993 in Fort Myers, Fla. Following the radiation treatment, the cuttings were rooted and terminal apices were removed (pinched) three times to promote lateral branch development. After lateral branches from the third pinch reached sufficient size, 500 terminal cuttings were harvested, planted and flowered in a controlled environment in Salinas, Calif. The cultivar Sunset Madison was discovered and selected by the inventor as a single flowering plant within this population in January, 1994. The selection of this plant was based on its desirable inflorescence form and floret colors and good post-production longevity. Asexual reproduction of the new cultivar by terminal cuttings taken in a controlled environment in Salinas, Calif., has shown that the unique features of this Chrysanthemum are stable and reproduced true to type in successive generations.

The cultivar Sunset Madison has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunset Madison'. These characeristics in combination distinguish 'Sunset Madison' as a new and distinct cultivar:

1. Upright and mounded plant habit.
2. Medium-size daisy spray-type inflorescences that are 6.4 to 7.3 cm in diameter.
3. Attractive red and yellow bi-colored ray florets and bright yellow disc florets.
4. Good postproduction longevity with inflorescences maintaining good substance and color for about 2.5 weeks in an interior environment.

The new Chrysanthemum differs fromt he its parent, the Chrysanthemum cultivar Madison, in ray floret color as plants of the cultivar Madison have white and purple bi-colored ray florets. In all other plant and inflorescence characteristics, plants of the new Chrysanthemum and the cultivar Madison are similar.

The accompanying colored photograph illustrates the overall appearance of the new cultivar, showing the colors as true as it is reasonably possible to obtain in colored reproductions of this type. The photograph comprises a top perspective view of a typical flowering plant of 'Sunset Madison'. Floret and foliage colors in the photograph may differ from the actual colors due to light reflectance.

In the following description, color refrences are made to The Royal Horticultural Society Colour Chart except where general terms of ordinary dictionary significance are used. The following observations and measurements describe plants grown in Leaminton, Ontario, Canada, under greenhouse conditions which approximate those generally used in commercial potted chrysanthemum production. Four unrooted cuttings were directly stuck in a 15-cm container. Measurements and numerical values represent averages for a minimum of four typical flowering containers.

Botanical classification: *Dendranthema grandiflora* cultivar Sunset Madison.

Commercial classification: Daisy spray-type pot chrysanthemum.

Parentage: Induced mutation of *Dendranthema grandiflora* cultivar Madison (U.S. Plant Pat. No. 9,313).

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous daisy spray-type pot Chrysanthemum. Upright, mounded habit and freely branching. Four to five lateral branches develop after removal of terminal apex (pinching).

*Plant height.*—23 to 28 cm.

*Foliage description.*—Leaf arrangement: Alternate. Leaf size, fully expanded: Length: About 9 cm. Width: About 4.5 cm. Leaf apex: Mucronate. Leaf base: Attenuate. Leaf margin: Palmately lobed, lobes converging. Leaf texture: Abaxial and adaxial surfaces slightly pubescent. Veins prominent on abadial surface. Color: Young foliage adaxial surface: 147A. Young foliage abaxial surface: 147B. Mature foliage adaxial surface: 147A. Mature foliage abaxial surface: 147B. Venation adaxial surface: 147B. Venation abaxial surface: 147B.

Inflorescence description:

*Appearance.*—Daisy spray-type inflorescence form with red and yellow bi-colored ray florets and bright yellow disc florets. Inflorescences borne on terminals above foliage, arising from leaf axils. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at lest 13.5 hours of darkness). Plants exposed to 1.5 to 2 weeks of long day/short night conditions after planting followed by photoinductive short day/long night conditions flower about 50 to 58 days later.

*Postproduction longevity.*—In an interior environment, inflorescences of cut flowering stems will maintain good color and substance for about 2.5 weeks in an interior environment.

*Quantity of inflorescences.*—Freely flowering with about 8 inflorescences per flowering lateral stem, or 32 to 40 inflorescences per plant.

*Inflorescence size.*—Diameter: 6.4 to 7.3 cm. Depth (height): About 9 mm. Diameter of disc: About 1.7 cm.

*Ray florets.*—Shape: Narrowly oblong, straight, very short corolla tube. Size: Length: About 2.8 cm. Width: About 1 cm. Apex: Acute. Margin: Entire. Texture: Smooth, glabrous. Aspect: Concave. Orientation: Positioned about 60° to the peduncle, upright. Number of ray florets per inflorescence: About 27.

*Color.*—Adaxial surface: Margin: 13A. Center: 34A. Abaxial surface: 13A tinged with 34A.

*Disc florets.*—Shape: Tubular. Size: Length: About 5 mm. Width: About 1 mm. Number of disc florets per inflorescence: About 194. Color: Immature: 154A. Mature: Apex: 14A. Base: 154A.

*Peduncle.*—Aspect: Flexible, angled about 45° to the stem. Length: First Peduncle: About 1.7 cm. Fourth peduncle: About 3.7 cm. Texture: Pubescent. Color: 143A.

*Reproductive organ.*—Androecium: Present on disc florets only. Anther color: 14A. Pollen: Moderate, 14A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Sunset Madison', as illustrated and described.

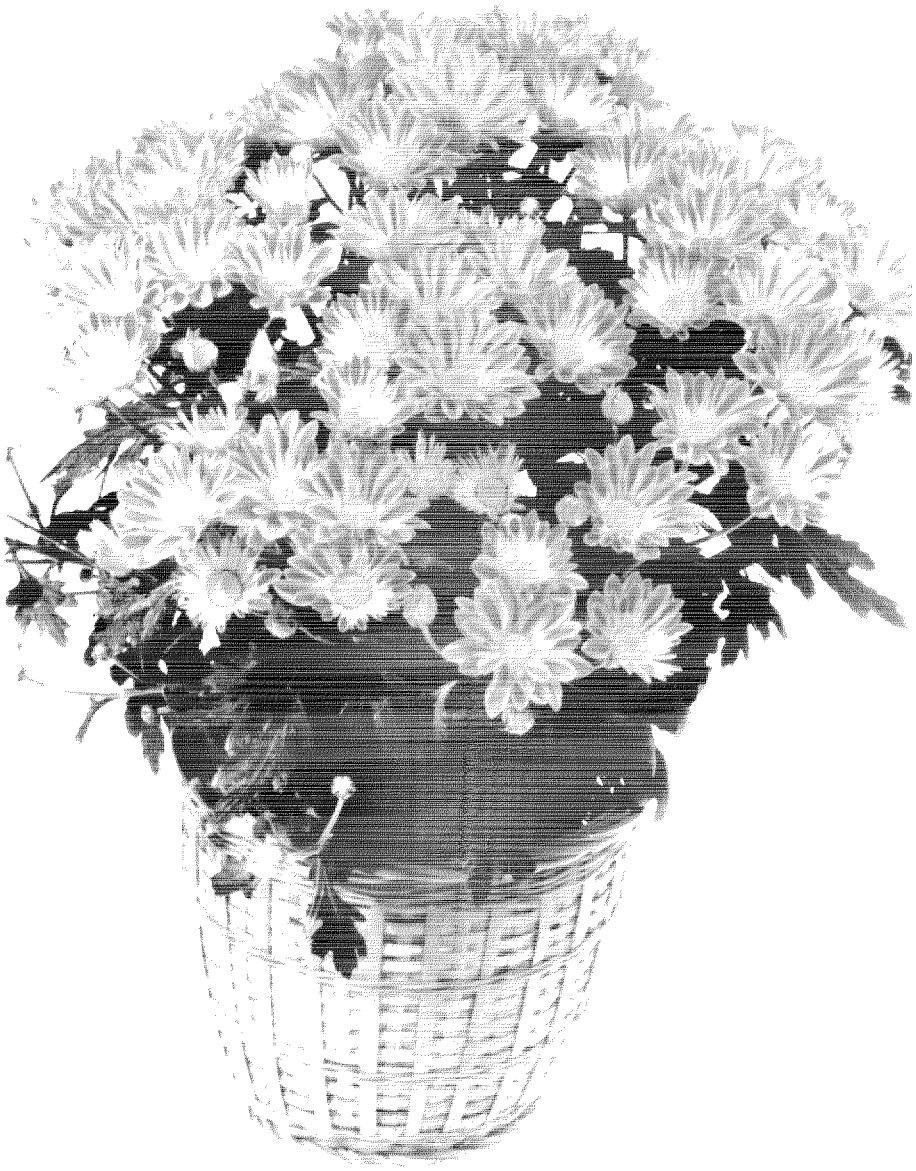

* * * * *